(12) United States Patent
Eicher et al.

(10) Patent No.: US 7,802,568 B2
(45) Date of Patent: *Sep. 28, 2010

(54) CARTRIDGE FOR A LIQUID

(75) Inventors: Joachim Eicher, Dortmund (DE);
Johannes Geser, Dortmund (DE);
Matthias Hausmann, Dortmund (DE);
Michael Schyra, Wuppertal (DE);
Gilbert Wuttke, Dortmund (DE);
Andreas Fiol, Wuppertal (DE);
Heinrich Kladders, Muelheim (DE);
Dieter Hochrainer, Bingen am Rhein (DE); Bernd Zierenberg, Bingen am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/232,896

(22) Filed: Sep. 23, 2005

(65) Prior Publication Data

US 2006/0016449 A1    Jan. 26, 2006

Related U.S. Application Data

(63) Continuation of application No. 09/511,267, filed on Feb. 23, 2000, now Pat. No. 6,988,496.

(60) Provisional application No. 60/165,915, filed on Nov. 17, 1999.

(30) Foreign Application Priority Data

Feb. 23, 1999    (DE)    ................... 199 40 713
Aug. 26, 1999    (MY)    ................... PI 99 00627

(51) Int. Cl.
*A61M 11/00*    (2006.01)
*A61M 15/00*    (2006.01)

(52) U.S. Cl. ............... 128/200.14; 128/202.27; 128/203.21; 239/271; 239/272; 222/81

(58) Field of Classification Search ............ 128/200.11, 128/200.14, 200.22, 203.12, 203.19, 203.21, 128/203.28, 204.14, 205.13, 205.14, 205.15, 128/205.16, 205.17; 239/271, 272, 328; 222/80, 81, 82, 83, 83.5, 92, 94

See application file for complete search history.

(56) References Cited

U.S. PATENT DOCUMENTS 2,629,421 A * 2/1953 Ayres ........................ 72/360

(Continued)

FOREIGN PATENT DOCUMENTS

AU    4552085    1/1986

(Continued)

*Primary Examiner*—Justine R Yu
*Assistant Examiner*—Clinton Ostrup
(74) *Attorney, Agent, or Firm*—Michael P. Morris; Mary-Ellen M. Devlin; David L. Kershner (57) ABSTRACT

For meteredly dispensing a liquid over a period of several months from a container which can be stored over a long period of time, the need is for a container which is practically diffusion-tight and in which the liquid does not come into contact with the ambient atmosphere. The cartridge according to the invention is a three-shell container comprising a collapsible bag which contains the liquid, a container which is stable in respect of shape and a stiff metal casing. The cartridge can be releasably connected to a dispensing device. The cartridge can be provided with a micro-opening with which the time for pressure equalisation between the cartridge and the ambient atmosphere can be adjusted. The cartridge is suitable for aqueous and for alcoholic liquids which contain a pharmaceutically active substance. The liquid in the cartridge is protected from external influences. The cartridge can be used in an atomiser for producing an inhalable aerosol for the treatment of illnesses.

8 Claims, 4 Drawing Sheets

U.S. PATENT DOCUMENTS

| | | |
|---|---|---|
| 3,255,972 A | 6/1966 | Hultgren et al. |
| 3,656,660 A * | 4/1972 | Mueller .................. 222/94 |
| 3,878,977 A | 4/1975 | Carlisle |
| 4,045,860 A | 9/1977 | Winckler |
| 4,093,124 A * | 6/1978 | Morane et al. .............. 239/327 |
| 4,116,336 A | 9/1978 | Sorensen et al. |
| 4,162,030 A | 7/1979 | Capra |
| 4,264,018 A | 4/1981 | Warren |
| 4,322,020 A | 3/1982 | Stone |
| 4,440,316 A | 4/1984 | Christine |
| 4,457,454 A | 7/1984 | Meshberg |
| 4,457,455 A | 7/1984 | Meshberg |
| 4,469,250 A | 9/1984 | Evezich |
| 4,479,989 A | 10/1984 | Mahal |
| 4,526,823 A | 7/1985 | Farrell et al. |
| 4,559,052 A | 12/1985 | Babson |
| 4,592,475 A * | 6/1986 | Hannon et al. .............. 215/252 |
| 4,637,934 A | 1/1987 | White |
| 4,732,299 A | 3/1988 | Hoyt |
| 4,760,937 A * | 8/1988 | Evezich .................. 222/95 |
| 4,817,830 A | 4/1989 | Yavorsky |
| 5,004,123 A | 4/1991 | Stoody |
| 5,012,956 A * | 5/1991 | Stoody .................. 222/94 |
| 5,031,384 A | 7/1991 | Rebeyrolle et al. |
| 5,038,951 A * | 8/1991 | Rizzardi .................. 215/256 |
| 5,102,010 A | 4/1992 | Osgar et al. |
| 5,105,995 A | 4/1992 | Martin |
| 5,129,894 A | 7/1992 | Sommermeyer et al. |
| 5,137,175 A | 8/1992 | Kowalski et al. |
| 5,158,810 A | 10/1992 | Oishi et al. |
| 5,176,178 A | 1/1993 | Schurter et al. |
| 5,213,227 A | 5/1993 | Koyama et al. |
| 5,242,085 A | 9/1993 | Richter et al. |
| 5,275,311 A * | 1/1994 | Piarrat .................. 222/209 |
| 5,289,818 A | 3/1994 | Citterio et al. |
| 5,292,033 A | 3/1994 | Gueret |
| 5,316,221 A | 5/1994 | Glover et al. |
| 5,332,121 A | 7/1994 | Schmidt et al. |
| 5,337,740 A * | 8/1994 | Armstrong et al. ..... 128/203.12 |
| 5,355,872 A | 10/1994 | Riggs et al. |
| 5,370,272 A | 12/1994 | Gueret |
| 5,385,251 A | 1/1995 | Dunn |
| 5,395,365 A | 3/1995 | Weiler et al. |
| 5,421,485 A | 6/1995 | Furuta et al. |
| 5,480,067 A | 1/1996 | Sedlmeier |
| 5,497,909 A | 3/1996 | Wirsig et al. |
| 5,507,409 A | 4/1996 | Paradine |
| 5,509,578 A | 4/1996 | Livingstone |
| 5,514,123 A | 5/1996 | Adolf et al. |
| 5,520,972 A | 5/1996 | Ezaki et al. |
| 5,520,975 A | 5/1996 | Inoue et al. |
| 5,562,219 A * | 10/1996 | de Pous et al. .............. 215/274 |
| 5,579,760 A | 12/1996 | Kohler |
| 5,642,838 A | 7/1997 | Stoody |
| 5,730,328 A | 3/1998 | Maeder et al. |
| 5,752,629 A | 5/1998 | Hardy |
| 5,772,080 A | 6/1998 | de Pous et al. |
| 5,813,570 A | 9/1998 | Fuchs et al. |
| 5,833,088 A * | 11/1998 | Kladders et al. ............ 215/248 |
| 5,873,491 A | 2/1999 | Garcia et al. |
| 5,875,936 A | 3/1999 | Turbett et al. |
| 5,878,915 A | 3/1999 | Gordon et al. |
| 5,884,759 A * | 3/1999 | Gueret .................. 206/222 |
| 5,893,484 A | 4/1999 | Fuchs et al. |
| 5,894,841 A | 4/1999 | Voges |
| 5,910,138 A | 6/1999 | Sperko et al. |
| 5,944,217 A | 8/1999 | Baena |
| 5,968,619 A | 10/1999 | Carmen et al. |
| 6,013,363 A | 1/2000 | Takahashi et al. |
| 6,062,213 A | 5/2000 | Fuisz et al. |
| 6,062,430 A | 5/2000 | Fuchs |
| 6,073,807 A | 6/2000 | Wilford et al. |
| 6,109,315 A | 8/2000 | Stern |
| 6,129,236 A | 10/2000 | Osokin et al. |
| 6,223,933 B1 | 5/2001 | Hochrainer et al. |
| 6,244,472 B1 * | 6/2001 | Hennemann ........... 222/189.09 |
| 6,250,508 B1 | 6/2001 | Geser et al. |
| 6,280,431 B1 | 8/2001 | Domkowski et al. |
| 6,286,700 B1 | 9/2001 | Davidson |
| 6,364,163 B1 | 4/2002 | Mueller |
| 6,390,332 B2 | 5/2002 | Wakayama |
| 6,685,691 B1 | 2/2004 | Freund et al. |
| 6,918,547 B2 | 7/2005 | Jaeger et al. |
| 6,932,789 B2 | 8/2005 | Zierenberg et al. |
| 6,988,496 B1 * | 1/2006 | Eicher et al. ........... 128/200.14 |
| 2001/0009151 A1 | 7/2001 | Hochrainer |
| 2002/0007155 A1 | 1/2002 | Freund et al. |

FOREIGN PATENT DOCUMENTS

| | | |
|---|---|---|
| DE | 3446697 | 6/1986 |
| EP | 0 114 964 | 8/1984 |
| EP | 0 182 094 | 5/1986 |
| EP | 0 368 112 A2 | 11/1988 |
| EP | 0 315 440 B1 | 5/1989 |
| EP | 0 322 980 | 7/1989 |
| EP | 0 368 112 | 5/1990 |
| EP | 0 495 330 A1 | 7/1992 |
| EP | 0 585 908 A2 | 3/1994 |
| EP | 0 620 165 B1 | 10/1994 |
| EP | 0 621 027 B1 | 10/1994 |
| EP | 0 622 311 A2 | 11/1994 |
| EP | 0 629 165 B1 | 12/1994 |
| EP | 0 635 254 B1 | 1/1995 |
| EP | 0 653 359 B1 | 5/1995 |
| EP | 0 654 419 A1 | 5/1995 |
| EP | 0 763 482 A1 | 3/1997 |
| EP | 0 812 625 A2 | 12/1997 |
| WO | WO 92/16439 | 10/1992 |
| WO | WO 95/15895 | 6/1995 |
| WO | WO 97/01329 | 1/1997 |
| WO | WO 97/06842 | 2/1997 |
| WO | WO 97/12687 | 4/1997 |
| WO | WO 97/18143 | 5/1997 |
| WO | WO 98/27959 | 7/1998 |
| WO | WO 98/48943 | 11/1998 |
| WO | WO 99/43571 | 9/1999 |
| WO | WO 00/27543 | 5/2000 |
| WO | WO 00/49988 | 8/2000 |

* cited by examiner

CARTRIDGE FOR A LIQUID

CROSS REFERENCE TO RELATED APPLICATIONS

This application is a continuation of U.S. application Ser. No. 09/511,267, filed Feb. 23, 2000, now allowed, which claims the benefit under 35 U.S.C. §119(e) to provisional application No. 60/165,915, filed Nov. 17, 1999, the entire disclosures of which are herein incorporated by reference in their entirety.

BACKGROUND OF THE INVENTION

1. Field of the Invention

The invention concerns a cartridge for a liquid, which can be connected to a draw-off or dispensing device. The dispensing device includes an upper portion which accommodates the cartridge and a lower portion which can be pushed on over the connected cartridge. The upper portion of the device is provided with a connecting portion for the cartridge and with a dispensing connection portion for drawing off and dispensing the liquid.

Liquids in accordance with the present invention can be solutions, suspensions or emulsions, Preferred liquids are those which contain an active substance. Active substances can be pharmacologically active substances for treatment of the human or animal body or active substances for diagnostic purposes or for a cosmetic use.

The invention aims to adapt an economically manufacturable cartridge of that kind to specific demands.

2. Background Art

Different thin-wall containers of the general kind set forth, for a liquid, are known, which are not diffusion-tight in relation to volatile constituents of the liquid. In that case a part of the liquid is lost by diffusion and the level of concentration of constituents of the liquid changes in a manner which is possibly unacceptable. Containers of that kind are suitable for a relatively short storage time. In the case of other containers of the general kind set forth, unacceptable changes in the liquid occur due to diffusion or due to the action of air, prior to or during the period of use. Particularly in the case of containers for a liquid which contains medical active substances, there is a need to satisfy intensified demands in order to avoid unacceptable adverse effects on the quality of the medicament.

Accordingly the object of the invention is to develop a cartridge for a liquid, which can be economically produced even in large numbers and which in the filled condition can be stored over a long period of time even under difficult conditions. The invention seeks to provide that the liquid can be easily drawn off and not involve contact with the environment. The invention further seeks to provide that the cartridge can be connected to a draw-off or dispensing device as easily as possible and interchangeably and that the cartridge can be reliably handled even by unskilled persons, The invention further seeks to provide that the cartridge is also suitable for a liquid which contains medical active substances and satisfies the intensified conditions which occur in that situation.

BRIEF SUMMARY OF THE INVENTION

In accordance with the invention that object is attained by a cartridge which can be connected to a draw-off or dispensing device. The dispensing device includes an upper portion which accommodates the cartridge and a lower portion which can be pushed on over the connected cartridge. The upper portion of the device is provided with a connection portion for the cartridge and with a draw-off or dispensing connection portion for drawing off the liquid. The cartridge can be in the form of a triple-shell container comprising an outer stiff casing, a container which is stable with respect to shape and which is disposed in the casing; and a collapsible bag which is arranged in the container that is stable with respect to shape and which contains the liquid. The stiff casing can have a bottom which can be provided with an opening. The container which is stable with respect to shape can also have an opening and can be closed with a stopper provided with an insertion connection portion. The stopper can form a sealingly closing, centered guide means for the draw-off connection portion. The stopper can be non-releasably connected by the stiff casing to the container which is stable with respect to shape. The cartridge can be releasably connected to the connection portion at the upper portion of the dispensing device.

The connection between the cartridge and the connection portion of the device can be in the form of a plug-in connection, a screw connection or a bayonet connection. This connection can preferably be a releasable connection. Optionally, it can be in the form of a non-releasable connection or a connection which is difficult to release.

The stopper can preferably comprise a thermoplastic material and can be connected to the container that is stable with respect to shape, in force-locking and positively locking relationship, by means of a snap-action connection. The stopper can also be non-releasably welded to the container that is stable in respect of shape and that comprises thermoplastic material, by the materials merging together. The stopper can be provided in the insertion connection portion with a funnel-shaped centred guide means for the dispensing or draw-off connection portion. The guide means can be provided with guide ribs. The stopper can sealingly embrace the draw-off connection portion and can be in the form of a press fit for the latter. It may be desirable for the end of the insertion connection portion, that is towards the internal space of the collapsible bag, to be closed by a diaphragm which can be arranged inclinedly relative to the axis of the insertion connection portion and which can be pierced when the draw-off connection portion is introduced into the cartridge. That diaphragm prevents the liquid from escaping into the insertion connection portion during storage of the cartridge.

A sealing disc which can be provided with sealing beads or ridges can be provided between the upper edge of the container which is stable with respect to shape, and the inside of the stopper. The inside of the stopper can be provided with a sealing lip or a plurality of sealing lips which are pressed into the sealing disc on the upper edge of the container which is stable with respect to shape.

Apart from its opening, the stiff casing is diffusion-tight in relation to gases and liquids. This casing can be a one-piece deep-drawn metal casing, preferably of aluminum. The stiff casing can also be of a two-piece construction; then, the two parts of the casing are joined together and sealed off relative to each other by way of sealing elements by welding or by adhesive. The stiff casing can also comprise a plastic material, preferably a thermoplastic material.

The stiff casing can have a projecting bead or ridge at the edge of its bottom. The bottom can be provided with a recess which is arranged centrally as an inwardly turned region of the bottom.

The stiff casing preferably has at the center point of the bottom an opening which can be in the form of a bore. It is additionally possible to provide in the recess in the bottom of the casing an insert which preferably comprises plastic material and which includes an opening in the form of a micro-opening which communicates with the opening in the bottom of the stiff casing. A filter can be disposed in front of the micro-opening within the insert.

The opening in the bottom of the stiff casing can be of a diameter of between 0.1 mm and 5 mm when the cross-section involved is circular. The micro-opening in the insert, when a circular cross-section is involved, is between 10 pm and 500 pm in diameter and between 100 pm and 5000 pm in length. The micro-opening makes it possible to adjust to a desired value the time for pressure equalization between the internal space in the cartridge and its environment.

The stiff casing of metal can be provided in the proximity of its open end with a peripherally extending crease which embraces the stopper in force-locking and positively locking relationship. The stiff casing of thermoplastic material can be welded to the stopper, with merging of the materials thereof. In addition in its upper part the stiff casing can be provided with a peripherally extending, outwardly open groove which extends around the lower edge of the stopper. At its open end the stiff casing may have a flanged-over portion which embraces the upper edge of the stopper.

The stiff casing can be provided with a plurality of projections which protrude into the interior of the casing and which support the container which is stable in respect of shape within the stiff casing. Preferably three projections are disposed in the middle to the lower region of the stiff casing, which are disposed in a plane which is perpendicular to the axis of the casing. In the case of a stiff casing of metal, those projections can be produced when flanging the open end of the stiff casing.

The cartridge can be sealed in the region of the stopper with a-possibly diffusion-tight-sealing foil which closes the open end of the insertion connection portion. The outside of the casing bottom can also be provided with a-possibly diffusion-tight-sealing foil which covers over the opening in the bottom or the insert in the bottom of the casing. Both sealing foils prevent the penetration of dirt into the openings beneath the foils and prevent the diffusion of constituents of the liquid during the time for which the cartridge is stored. Both sealing foils are detached or pierced only immediately prior to first regular use of the cartridge.

The releasable connection between the cartridge and the connection portion of the dispensing device can be a plug-type connection in which the connection portion is provided with a plurality of snap hooks which engage into the peripherally extending groove in the upper part of the stiff casing after the cartridge has been inserted into the device. The plug connection can advantageously also be used for other containers of the general kind set forth, in which case the container which is stable in respect of shape or the stopper includes a groove into which the snap hooks engage.

Snap hooks of plastic material can be provided with a metal spring element which maintains the spring property of the snap hooks over a long period of time and at elevated temperature.

A free space which is covered by the sealing foil can be provided in the central region of the sealing foil on the outside of the bottom of the casing. A rigid or resilient piercing device can be disposed on the inside of the bottom of the lower portion of the device, the piercing device piercing the sealing foil disposed on the underside of the bottom of the casing, prior to the first withdrawal of a part of the liquid from the cartridge. That opens the opening in the bottom of the casing or the micro-opening in the insert and permits air to pass into the space inside the cartridge.

To remove a used cartridge from the dispensing device, it is possible to use a withdrawal aid which is pushed under the bead or ridge at the bottom of the stiff casing, thereby to make it easier to pull the cartridge out.

Before the cartridge is connected to the dispensing device, the sealing foils on the stopper and on the bottom of the cartridge are detached or those sealing foils are pierced when the cartridge is connected to the dispensing device. A difference in pressure which possibly prevails between the interior of the cartridge and the environment around the cartridge is equalized through the opening in the bottom of the stiff casing.

When a quantity of liquid is drawn out of the cartridge connected to the dispensing device, the collapsible bag collapses and its volume is reduced by the volume of the quantity of liquid which is drawn off. As a result there is a reduced pressure in the gas space of the cartridge (this is the free space between the outside of the collapsible bag and the inside of the stiff casing) in comparison with the pressure in the ambient atmosphere around the cartridge. That pressure difference is equalized in a relatively short period of time if the stiff casing is thin-walled and is provided with a bore in the region of between 0.1 mm and 5 mm.

If the cartridge is provided in the bottom of the stiff casing with an insert which includes a micro-opening, it is possible to adjust the time for pressure equalization between the gas space in the cartridge and the ambient atmosphere. For example with a volume of 3 milliliters of the gas space in the cartridge and a pressure difference of 20 hPa (20 mbar) between the ambient atmosphere around the cartridge and the gas space in the cartridge, in the case of a circular micro-opening of a length of 200 pm and a diameter of between 80 pm and 50 pm, it is possible to achieve a half-value time for pressure equalization of between 2 hours and 13 hours.

In the case of a pressure equalization time which is adapted to the usual time interval between two operations of drawing off liquid from the cartridge, the diffusion of constituents of the liquid out of the collapsed bag is made more difficult.

The cartridge according to the invention can be for example 55 mm in length and 17 mm in diameter. The stopper can have an insertion connection portion whose inside diameter gives a firm press fit on a dispensing connection portion of an outside diameter of 2 mm.

The cartridge according to the invention can be used in an atomizer as is shown n FIGS. 6a and 6b in WO-97/12687. The cartridge (1) of the present invention corresponds to the supply container (71) in FIGS. 6a and 6b, the spring portion of the locking clamping mechanism, in the form of connection portion (2), corresponds to the spring portion (56), and the lower portion (3) of the device corresponds to the lower housing portion (70).

The cartridge may contain an aqueous or alcoholic liquid.

When an aqueous liquid is involved, the container which is stable with respect to shape and the stopper can comprise polypropylene. The collapsible bag can comprise polyethylene. The stiff casing can comprise plastic material, preferably polypropylene. The opening in the bottom of the stiff casing can be a bore. The stopper for the container which is stable with respect to shape can be provided with an insertion connection portion which, at its end towards the internal space, can be closed with a diaphragm which is inclined relative to the axis of the insertion connection portion. The insertion connection portion can involve a press fit for the dispensing connection portion. The stopper can be connected to the container which is stable with respect to shape by a snap connection. The releasable plug-in connection between the cartridge and the connection portion of the dispensing device can be a snap connection in which the snap hooks in the connection portion of the dispensing device engage into the peripherally extending groove in the upper region of the cartridge the inside of the bottom of the lower portion of the device which is fitted on the upper portion can be provided with a resilient piercing device for the sealing foil on the underside of the bottom of the casing.

In the case of an alcoholic liquid the container which is stable with respect to shape and the stopper can comprise polypropylene. The collapsible bag can comprise polyethylene. The stiff casing can comprise metal, preferably aluminum. The recess in the bottom of the stiff casing may receive an insert with a micro-opening which communicates with the bore in the bottom of the casing. The stopper provided with an insertion connection portion, for the container which is stable with respect to shape, can be closed at its end towards the internal space by a diaphragm which is inclined with respect to the axis of the insertion connection portion. The insertion connection portion can be provided with a sealing closing centered guide means for the dispensing connection portion, the guide means being in the form of a press fit. The stopper can be non-releasably connected to the container which is stable with respect to shape, by means of the stiff casing. The releasable plug connection between the cartridge and the connection portion of the dispensing device can be a snap connection in which the snap hooks in the connection portion of the dispensing device engage into the peripherally extending groove in the upper region of the cartridge. The inside of the bottom of the fitted-on lower portion of the device can be provided with a resilient piercing device for the sealing foil on the underside of the bottom of the casing.

The cartridge according to the invention can be filled with a medical liquid which for example contains a pharmacologically active substance and for example water, ethanol or mixtures thereof.

WO-98/27959 describes stabilized aqueous medicament preparations for producing propellent gas-free aerosols for inhalation. Attention is directed to the formulations which are claimed therein and set forth in the Examples.

Suitable medicament preparations in an ethanol solution are set forth for example in WO-97/01329, and in particular attention is directed to the active substances referred to therein (see therein pages 2 and 3) and the stabilized formulations claimed therein.

As medical active substances it is possible to use Berotec (Fenoterol hydrobromide); 1-(3,5-dihydroxy-phenyl)-2-[[1-(4-hydroxy-benzyl)ethyl]-amino)-ethanol hydrobromide), Atrovent (Ipratropium bromide), Berodual (combination of Fenoterol hydrobromide and Ipratropium bromide), Salbutamol, Salbutamol sulphate, Combivent, Oxivent (Oxitropium bromide), Ba 679 (Tiotropium bromide), BEA 2108 (di-(2thienyl)-glycolic acid tropenol ester), Flunisolid, Budesonid, Beclomethasone and others.

The cartridge according to the invention enjoys the following advantages:

- The concentration of the medical liquid contained in the sealed cartridge varies only to a tolerable extent even over a storage time of several years and at elevated storage temperature.
- The content of the cartridge is highly effectively protected from contamination.
- The cartridge when fitted into the dispensing device can be used over several months.
- The half-value time for pressure equalization can be adjusted by the shape of the micro-opening.
- The cartridge can be produced in medically acceptable form.
- The unmodified original condition of the cartridge and the content thereof can be readily perceived within the specified period of usability by virtue of the intact sealing foils.
- The cartridge has a high degree of functional reliability; mishandling is avoided.
- The cartridge is securely held in the dispensing device.
- The fixedly closed cartridge is child-proof and makes it more difficult to manipulate the content thereof.
- The empty cartridge can be easily pulled out of the dispensing device because of the ridge at the bottom of the stiff casing.

Figure 1:
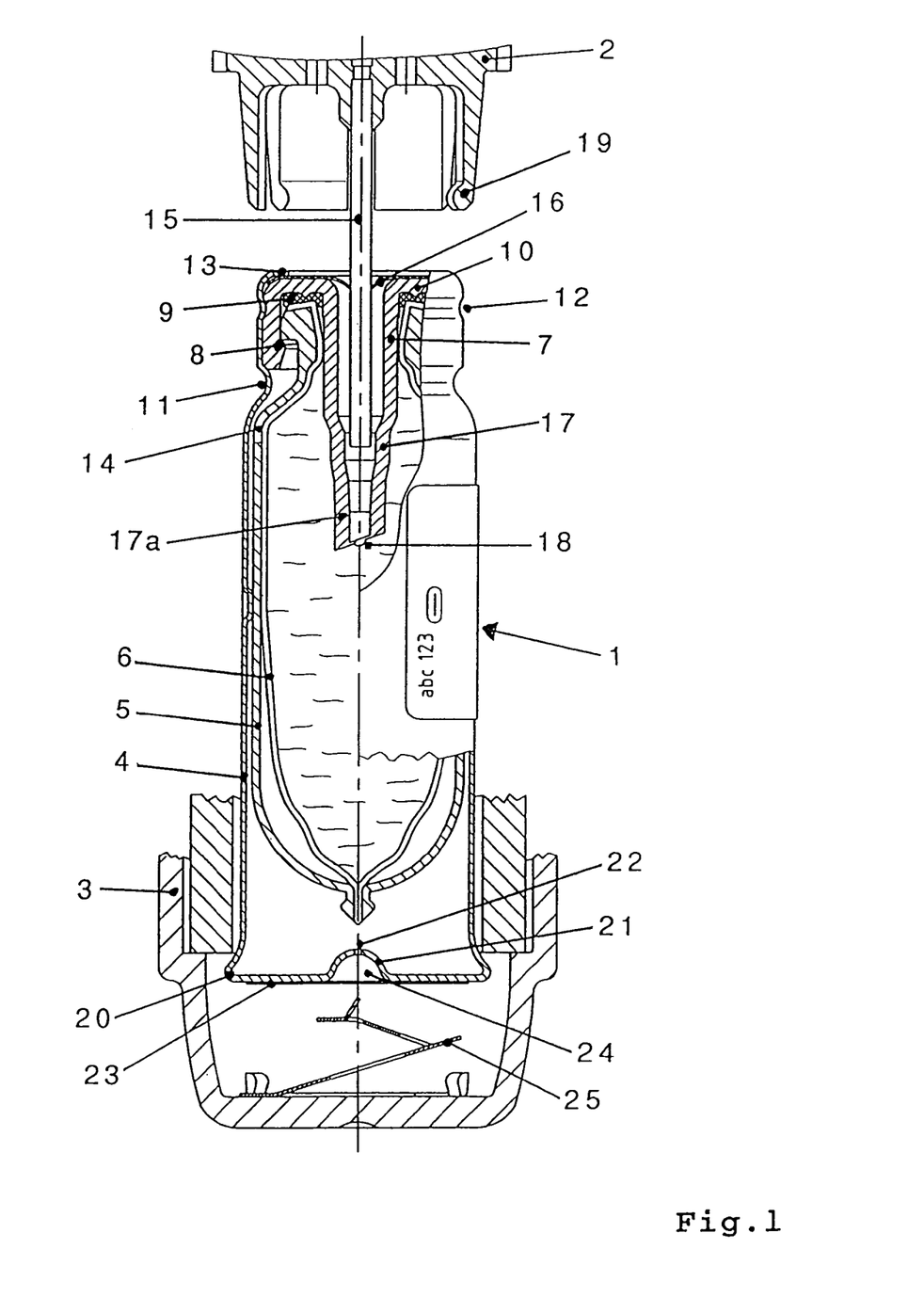

The cartridge according to the invention which contains a medical liquid can be used to produce an inhalable aerosol by means of an atomizer. The aerosol can serve for treating illnesses.

BRIEF DESCRIPTION OF THE DRAWINGS/FIGURES

FIG. 1 is a cross-sectional view of a cartridge of the present invention and a connection portion and lower portion of a draw-off of dispensing device connected to the cartridge.

FIG. 2 is a cross-sectional view as in FIG. 1, with the cartridge completely pushed into the connection portion and lower portion of the dispensing device.

FIG. **3*a*** is an enlarged cross-sectional view of the lower portion of the dispensing device and the lower end of the cartridge.

FIG. **3*b* is an enlarged cross-section view as in FIG. 3*a*** with the piercing device having pierced the sealing foil.

FIG. **4*a*** is a cross-section through a withdrawal aid fitted on the cartridge of the invention.

FIG. **4*b*** is a plan view of the withdrawal aid fitted onto the cartridge with the stiff over casing in cross-section.

DETAILED DESCRIPTION OF THE INVENTION

The cartridge according to the invention is described in greater detail by means of the drawings.

FIG. 1 shows the cartridge 1, the connection portion 2 of the draw-off or dispensing device and the lower portion 3 of the device which is pushed over the connected cartridge. The stiff casing 4 contains the container 5 which is stable with respect to shape, with the collapsible bag 6. The container 5 is closed by the stopper 7 and the snap connection 8. Disposed between the upper edge of the container 5 and the underside of the stopper 7 is the sealing disc 9 into which the sealing lip 10 is pressed. The stiff casing 4 includes the peripherally extending groove 11 against which the lower edge of the stopper 7 bears. The peripherally extending crease 12 in the stiff casing 4 is pressed into the stopper 7. The stopper 7 is held at its top side by the flanged-over portion 13 of the upper end of the stiff casing 4. The opening 14 is provided in the container 5.

The connection portion 2 of the dispensing device includes the dispensing or draw-off connection portion 15 which has already pierced the sealing foil 16 on the top side of the stopper 7 and which has penetrated into the insertion connection portion 17. When the cartridge 1 is further pushed onto the dispensing connection portion 15 it penetrates the region **17*a* of the press fit and pierces the inclined diaphragm 18 at the end of the insertion connection portion 17. The snap hooks 19 on the connection portion 2 of the dispensing device engage from the outside into the peripherally extending groove 11 in the stiff casing 4**.

The stiff casing 4 is provided in its central region with projections 4a which are disposed in a plane which is perpendicular to the axis of the casing. Those projections support the container 5.

The stiff casing 4 is provided at its bottom edge with the projecting ridge or bead 20. Disposed in the center of the recess in the form of the inwardly inverted region 21 is the opening 22 in the stiff casing 4. The bottom of the stiff casing 4 is covered by the sealing foil 23. The free space 24 is to be found between the sealing foil 23 and the inwardly curved region. The resilient piercing device 25 is disposed on the inside of the lower portion 3 of the dispensing device.

Figure 2:
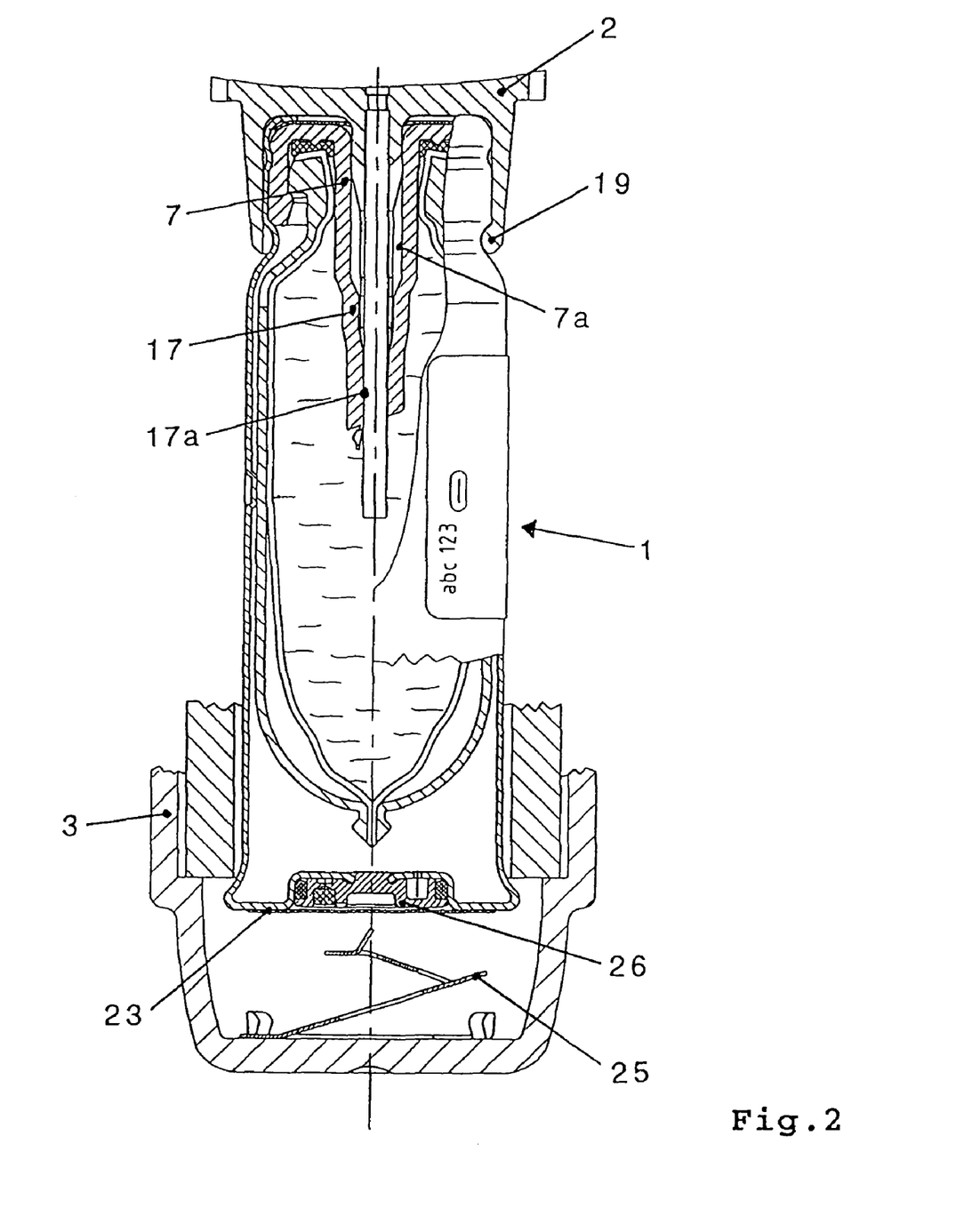

FIG. 2 shows the cartridge 1 when it has been completely pushed onto the dispensing connection portion 15 and connected to the connection portion 2. The inclined diaphragm 18 at the end of the insertion connection portion 17 is pierced and the snap hooks 19 engage into the peripherally extending groove 11 at the upper end of the stiff casing. The stopper 7 is provided with guide ribs 7a. The region 17a involves a press fit between the dispensing connection portion 15 and the stopper 7. The insert 26 is disposed in the recess in the form of the inwardly inverted region 21 of the bottom of the stiff casing 4.

Figure 3A:
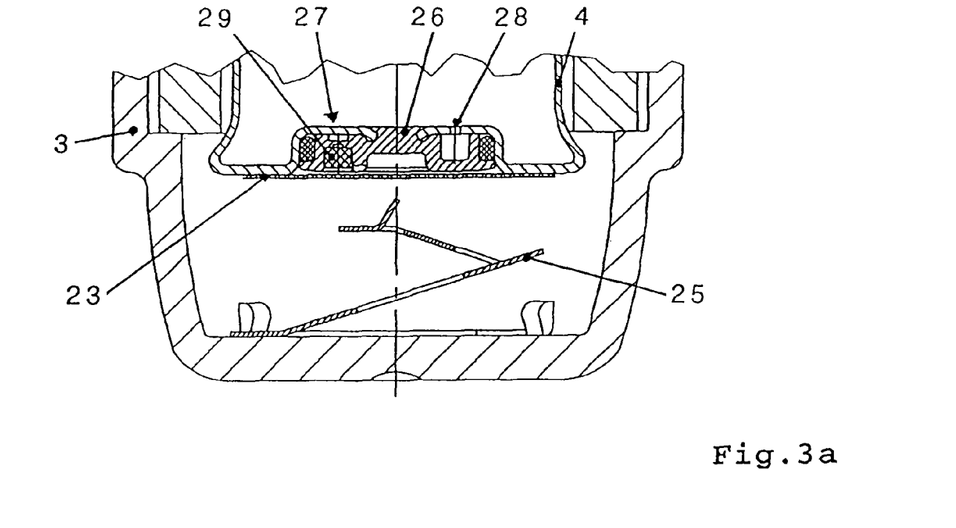

FIG. 3a shows the end of the stiff casing 4, the end of the lower portion 3 of the dispensing device and the insert 26 on an enlarged scale. The insert 26 includes the micro-opening 27 which communicates with the opening 28 in the bottom of the stiff casing 4. Disposed in front of the micro-opening is the filter 29. The bottom of the stiff casing is covered by the sealing foil 23.

Figure 3B:
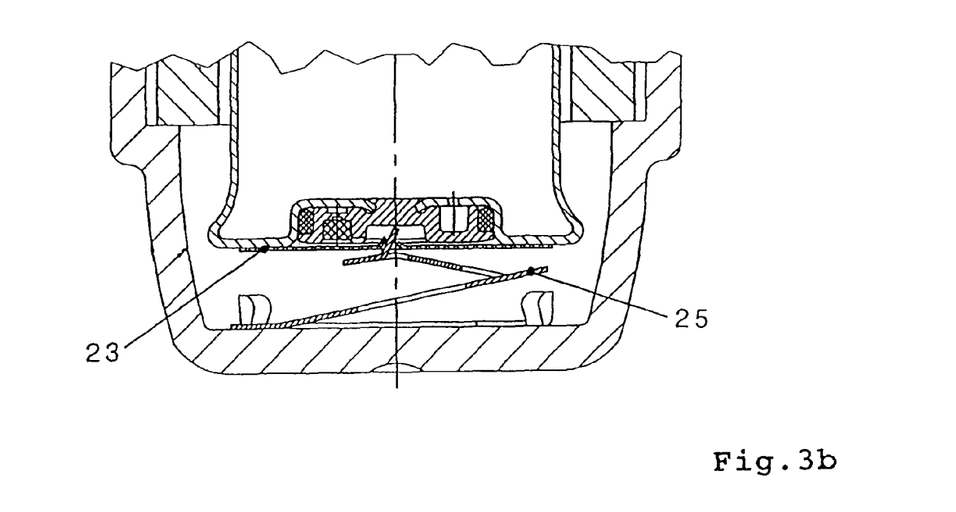

FIG. 3b shows the condition in which the piercing device 25 has pierced the sealing foil 23.

Figure 4A:
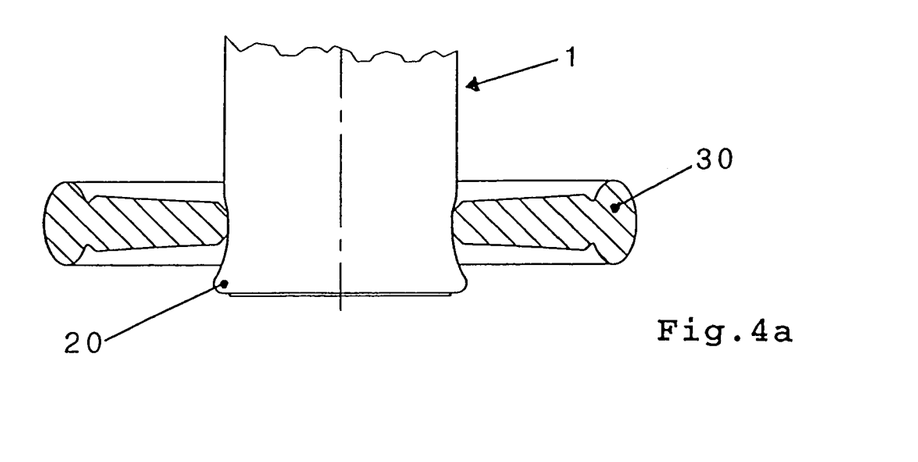

FIG. 4a shows a cross-section through the withdrawal aid 30 which is fitted onto the cartridge 1 and which has pressed the stiff casing 4 in, behind the ridge or bead 20. The cartridge 1 is clamped in position in the withdrawal aid 30 and can be turned about the axis of the cartridge and pulled out of the dispensing device by means of the withdrawal aid 30.

Figure 4B:
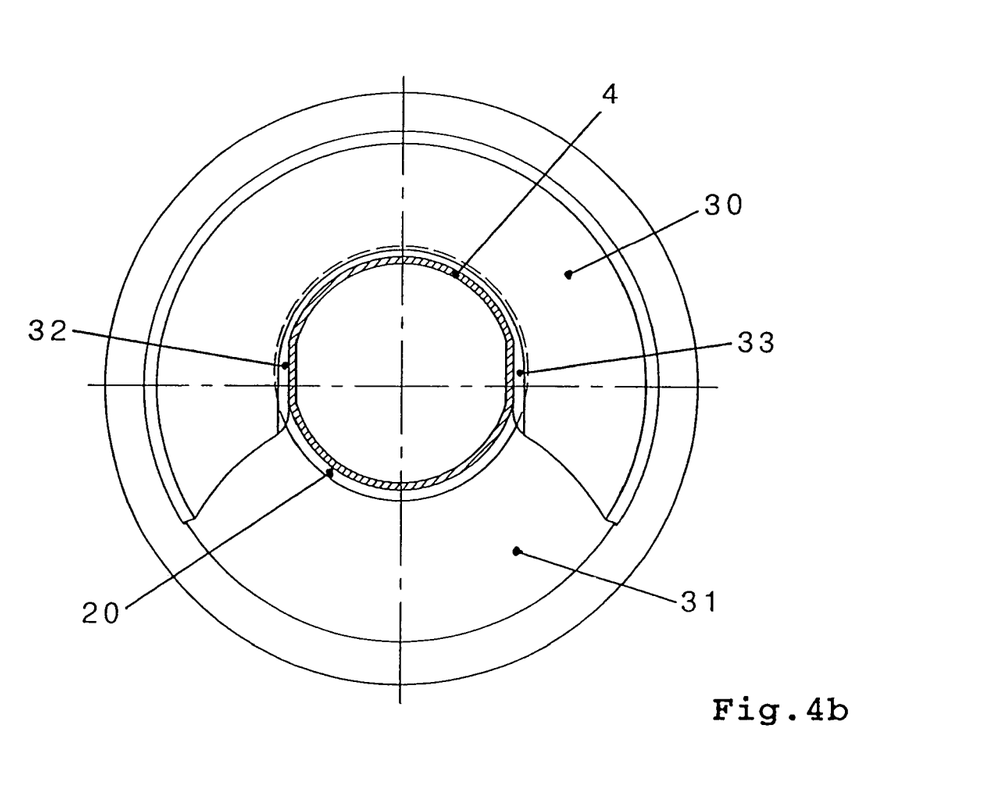

FIG. 4b shows a view from above of the withdrawal aid 30 in the condition of being fitted on the cartridge and the stiff casing 4 in cross-section. The withdrawal aid 30 includes an opening with a centrally arranged region whose diameter is substantially the same as the outside diameter of the stiff casing 4 and which is smaller than the diameter of the bead or ridge 20. The central region of the opening goes into an enlarged opening 31 so that the withdrawal aid 30 can be easily fitted onto the end of the cartridge. The diameter of the central region of the opening is reduced at two mutually diametrically oppositely disposed locations 32 and 33 and the circular arc of the opening is flattened. At those locations, the stiff casing of the cartridge is compressed when the withdrawal aid 30 is pushed on, whereby a tight connection is made between the withdrawal aid and the cartridge 1.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

What is claimed is:

1. A releasable connection between a cartridge and a connection portion of a dispensing device, the cartridge being interchangeable and including a stiff outer casing or a shape stable container or a stopper, the releasable connection comprising:

a connection portion disposed on an upper portion of the dispensing device and including a draw-off connection portion for drawing off a liquid contained in the cartridge; and a plurality of discrete snap hooks provided on the connection portion, wherein the connection portion is releasably secured to the cartridge by the snap hooks which individually engage into a peripherally extending groove in the stiff outer casing or the shape stable container or the stopper, after the casing or the container or the stopper has been pushed into the dispensing device, wherein the connection portion is configured to be reused with a second cartridge, wherein the connection portion is releasably secured to the second, cartridge by the snap hooks after the connection portion is released from engagement with the first cartridge, wherein the connection portion includes a plurality of vertical extensions, wherein each snap hook is provided on one of the plurality of vertical extensions, and wherein the draw-off connection portion vertically extends between the plurality of vertical extensions so as to be substantially surrounded by the plurality of snap hooks, and wherein the connection portion is a single-piece of material including the plurality of vertical extensions and the draw-off connection portion.

2. The releasable connection according to claim 1, wherein the snap hooks are made of plastic material and have a spring property.

3. The releasable connection according to claim 1, wherein a foil on a top-side of the cartridge is pierced by the draw-off connection portion when the casing or the container or the stopper is pushed into the dispensing device.

4. The releasable connection according to claim 1, wherein the draw-off connection portion penetrates into an insertion connection portion of the cartridge.

5. The releasable connection according to claim 4, wherein a diaphragm at an end of the insertion connection portion is pierced by the draw-off connection portion.

6. The releasable connection according to claim 4, wherein a collapsible bag is disposed in the cartridge and contains the liquid, wherein the insertion connection portion extends into an interior space of the collapsible bag, the liquid being drawn through the draw-off connection portion penetrating the insertion connection portion.

7. A releasable connection between a cartridge and a connection portion of a dispensing device, the cartridge including a stiff outer casing or a shape stable container or a stopper, the releasable connection releasably securing the cartridge to the connection portion, the releasable connection consisting essentially of:

a connection portion disposed on an upper portion of the dispensing device and including a draw-off connection portion for drawing off a liquid contained in the cartridge;

a plurality of vertical extensions provided on the connection portion and extending vertically downward from the connection portion; and a plurality of discrete snap hooks, wherein each snap hook is provided on one of the plurality of vertical extensions, wherein the connection portion is releasably secured to the cartridge by the snap hooks which individually engage into a peripherally extending groove in the stiff outer casing or the shape stable container or the stopper, after the casing or the container or the stopper has been pushed into the dispensing device, wherein the draw-off connection portion extends vertically downward between the plurality of vertical extensions so as to be substantially surrounded by the plurality of snap hooks, wherein the connection portion is a single-piece of material including the plurality of vertical extensions and the draw-off connection portion.

8. The releasable connection according to claim 7, wherein the cartridge is interchangeably connected to the connection portion, wherein the connection portion is releasably secured to a second cartridge by the snap hooks after the connection portion is released from engagement with the first cartridge.

* * * * *